United States Patent
Johansson et al.

(10) Patent No.: US 12,147,491 B2
(45) Date of Patent: Nov. 19, 2024

(54) COMPUTER-IMPLEMENTED METHOD, COMPUTER PROGRAM PRODUCT AND SYSTEM FOR DATA ANALYSIS

(71) Applicant: Sartorius Stedim Data Analytics AB, Umea (SE)

(72) Inventors: Erik Axel Johansson, Röböck (SE); Kleanthis Mazarakis, London (GB)

(73) Assignee: SARTORIUS STEDIM DATA ANALYTICS AB, Umea (SE)

( * ) Notice: Subject to any disclaimer, the term of this patent is extended or adjusted under 35 U.S.C. 154(b) by 53 days.

(21) Appl. No.: 17/586,525

(22) Filed: Jan. 27, 2022

(65) Prior Publication Data
US 2022/0237264 A1    Jul. 28, 2022

(30) Foreign Application Priority Data
Jan. 27, 2021   (EP) ..................... 21153693

(51) Int. Cl.
| | | |
|---|---|---|
| G06F 17/18 | (2006.01) | |
| G06F 17/16 | (2006.01) | |
| G06F 18/211 | (2023.01) | |
| G16B 50/30 | (2019.01) | |
| G16C 20/70 | (2019.01) | |

(52) U.S. Cl.
CPC .............. G06F 17/18 (2013.01); G06F 17/16 (2013.01); G06F 18/211 (2023.01); G16B 50/30 (2019.02); G16C 20/70 (2019.02)

(58) Field of Classification Search
CPC .................... G06F 17/18; G06F 17/16; G06F 18/21–2115; G16C 20/70
See application file for complete search history.

(56) References Cited

U.S. PATENT DOCUMENTS

2009/0164171 A1*  6/2009  Wold .................. G06F 18/2135
                                                              702/179

FOREIGN PATENT DOCUMENTS

EP        2235644        10/2010

OTHER PUBLICATIONS

Mehmood et al., "Comparison of variable selection methods in partial least squares regression" Journal of Chemometrics. 2020;34:e3226 (Year: 2020).*

(Continued)

*Primary Examiner* — John C Kuan
(74) *Attorney, Agent, or Firm* — Klarquist Sparkman, LLP

(57) ABSTRACT

A computer-implemented method for analyzing data obtained for a chemical and/or biological process comprises: obtaining a result of statistical data analysis on the data obtained with respect to the chemical and/or biological process; calculating, for values of process parameters obtained at groups of time points during batch processes of the chemical and/or biological process, a ratio of a correlation value to a confidence value of the correlation value, the correlation value indicating a correlation between the values of the process parameter and at a process output value; calculating, for process parameters, an average of absolute values of the ratios calculated for the values of the process parameter obtained at different groups of time points during the batch processes; excluding the values of one of the process parameters having a smallest average; and iterating, until at least one specified condition is met.

15 Claims, 11 Drawing Sheets

(56) References Cited

OTHER PUBLICATIONS

Li et al., "Bootstrap standard error and confidence intervals for the correlations corrected for indirect range restriction" British Journal of Mathematical and Statistical Psychology (2011), 64, 367-387 (Year: 2011).*
Roy et al., "On Some Aspects of Variable Selection for Partial Least Squares Regression Models" QSAR Comb. Sci. 27, 2008, No. 3, 302-313 (Year: 2008).*
Geladi et al., "Partial least-squares regression: a tutorial," Anal. Chim. Acta, vol. 185, No. Supplement C, pp. 1-17, Jan. 1986.
Wold et al., "Principal component analysis," Chemom. Intell. Lab. Syst., vol. 2, No. 1, pp. 37-52, Aug. 1987.
Wold et al., "PLS-regression: a basic tool of chemometrics," Chemom. Intell. Lab. Syst., vol. 58, No. 2, pp. 109-130, Oct. 2001.
Gauchi et al., "Comparison of selection methods of explanatory variables in PLS regression with application to manufacturing process data," Chemometrics and Intelligent Laboratory Systems 58 (2001), pp. 171-193.
Anzanello et al., "Selecting the best variables for classifying productions batches into two quality levels," Chemometrics and Intelligent Laboratory Systems 97 (2009), pp. 111-117.
Mehmood et al., "A review of variable selection methods in Partial Least Squares Regression," Chemometrics and Intelligent Laboratory Systems 118 (2012), pp. 62-69.
Extended European Search Report received in counterpart European Application No. 21153693.3, Jul. 21, 2021, 9 pages.
Examination Report, received in European Patent Application No. 21153693.3, May 19, 2023, 7 pages.

* cited by examiner

| Number of removed logical blocks | R2 | Q2 |
| --- | --- | --- |
| 0 | 0.8435 | 0.5875 |
| 1 | 0.8469 | 0.6106 |
| 2 | 0.8495 | 0.6333 |
| 3 | 0.8377 | 0.6333 |
| 4 | 0.8378 | 0.6291 |
| 5 | 0.8320 | 0.6389 |
| 6 | 0.8258 | 0.6202 |
| 7 | 0.8286 | 0.6237 |
| 8 | 0.8173 | 0.5955 |
| 9 | 0.8286 | 0.5818 |
| 10 | 0.8281 | 0.6031 |
| 11 | 0.8286 | 0.5940 |
| 12 | 0.8018 | 0.5505 |
| 13 | 0.7745 | 0.4667 |
| 14 | 0.7419 | 0.5092 |
| 15 | 0.7431 | 0.3222 |
| 16 | 0.7156 | 0.2753 |
| 17 | 0.7218 | 0.4594 |
| 18 | 0.6721 | 0.5778 |
| 19 | 0.4908 | 0.4003 |

| Logical blocks | Ratios of correlation values to confidence values |
|---|---|
| $CO_2$ | 4.78 |
| Base added | 3.30 |
| Glutamate | 2.78 |
| Glutamine | 2.40 |
| Lactate | 2.15 |
| qp | 2.07 |
| Ammonium | 1.95 |
| VCC | 1.94 |
| $pH_2$ | 1.75 |
| $pH_1$ | 1.62 |

FIG 9

COMPUTER-IMPLEMENTED METHOD, COMPUTER PROGRAM PRODUCT AND SYSTEM FOR DATA ANALYSIS

FIELD

The field relates to a computer-implemented method, a computer program product and a system for data analysis.

BACKGROUND

When monitoring and/or controlling chemical and/or biological processes, a huge amount of data may be collected and analyzed. For example, with respect to some chemical and/or biological processes, values of hundreds of parameters may be obtained (e.g., by measurements) during and/or after the processes. For analyzing the collected data, multivariate modeling methods may be employed. A multivariate modeling method may construct a model of a process, using a plurality of variables to predict an outcome of the process.

SUMMARY

According to an aspect, the problem relates to facilitating analysis of multivariate data. This problem is solved by the features disclosed by the independent claims. Further exemplary embodiments are defined by the dependent claims.

According to an aspect, a computer-implemented method is provided for analyzing data obtained with respect to a chemical and/or biological process. The method comprises:
obtaining a result of statistical data analysis on a data set including the data obtained with respect to the chemical and/or biological process, wherein:
the chemical and/or biological process is carried out in a plurality of batch processes having a finite duration,
values of process parameters relating to the chemical and/or biological process are obtained at a plurality of time points during each batch process, each time point in one of the plurality of batch processes having corresponding time points in other ones of the plurality of batch processes,
at least one process output value is obtained at or after an end of each batch process,
the data set includes, for each batch process, the values of the process parameters and the at least one process output value,
the result of the statistical data analysis includes, for the values of each process parameter obtained at each group of corresponding time points during the plurality of batch processes, a correlation value and a confidence value corresponding to a confidence interval of the correlation value, the correlation value indicating a correlation between:
the values of the process parameter obtained at the group of corresponding time points during the plurality of batch processes, and
the at least one process output value;
calculating, for the values of each process parameter obtained at each group of corresponding time points during the plurality of batch processes, a ratio of the correlation value to the confidence value;
calculating, for each process parameter, an average of absolute values of the ratios calculated for the values of the process parameter obtained at different groups of the corresponding time points during the plurality of batch processes;
excluding, from the data set, the values of one of the process parameters having a smallest one of the averages calculated for the process parameters; and
iterating, until at least one specified condition is met, the steps of obtaining the result of the statistical data analysis, calculating the ratio of the correlation value to the confidence value, calculating the average of the absolute values of the ratios and excluding the values of the one of the process parameters.

In the present disclosure, the "process parameters" may be parameters relating to a chemical and/or biological process, values of which may be obtained during the process. The values of the process parameters may be obtained by measuring the values during the process or by deriving the values from one or more measurements performed during the process. Examples of the "process parameters" may include, but are not limited to, temperature, pressure, pH, agitation, flow of a gas or liquid, an amount of a particular substance, etc. Further, in the present disclosure, the "process parameters" may be considered as parameters that may affect an outcome of the chemical and/or biological process.

In the present disclosure, the term "process output value" may be understood as a value of a parameter that relates to an outcome and/or a target of the chemical and/or biological process. The "process output value" may be measured or derived from one or more measurements at or after an end of the process. Examples of a parameter for the "process output value" may include, but are not limited to, yield in a chemical process, titer in a biological process, amount of a by-product, etc. In the present disclosure, the "process output value" or the parameter for the "process output value" may also be referred to as a "quality attribute" or a "critical quality attribute (CQA)".

In various aspects and embodiments described herein, in each of the "plurality of batch processes" carried out for a chemical and/or biological process, values of the process parameters may be obtained at a plurality of time points. In other words, the values of the process parameters may be obtained at a plurality of points in time during each of the plurality of batch processes. In some examples, the plurality of time points may occur in a specified time interval, e.g., every 10 minutes, every hour, every day, every other day, etc. In various aspects and embodiments described herein, at least some of the values of the process parameters may be measured at the plurality of time points. Additionally or alternatively, at least some of the values of the process parameters may be calculated from one or more measured values at the plurality of time points. In some circumstances, for at least one process parameter, a value may be measured (or calculated from one or more measured values) at a first time point of the plurality of time points and the measured or calculated value at the first time point of the plurality of time points may be used (e.g., obtained) as the value(s) of the at least one process parameter at one or more other time points following the first time point. As a specific example, a value may be measured or calculated for a process parameter at a specific time on one day (this may be considered as a first time point) and then the measured or calculated value may be maintained to be used as the value(s) of the process parameter at the subsequent time point(s) (e.g., with a time interval shorter than 24 hours) until the next measurement or calculation at the same specific time on the following day.

In some circumstances, the time interval in which the plurality of time points occur may vary within a batch process, e.g., every 10 minutes in the first half of the duration of the batch process and 20 minutes in the second half of the duration of the batch process. For instance, in case a batch process has two or more phases (e.g., in chromatography), the time interval for the time points may be different for different phases within the batch process.

In various aspects and embodiments described herein, the plurality of batch processes may have an identical number of time points occurring in a same specified time interval (with a certain error margin). In other words, the time points in the plurality of batch processes may be grouped into groups of corresponding timing in which the time points occur. For example, in case each batch process has L time points (TP_1, ..., TP_2, ..., TP_I, ..., TP_L), the l-th time point (l=1, 2, ..., L) in each of the plurality of batch processes may be considered as belonging to a same group of corresponding time points.

In the present disclosure, the values of each one of the plurality of process parameters, obtained at the plurality of time points during the plurality of batch processes, may be considered as belonging to a "logical block" corresponding to the one of the plurality of process parameters. Accordingly, the step of excluding, from the data set, the values of one of the process parameters having a smallest one of the averages calculated for the process parameters, as referred to in the above-stated aspect, may be understood as excluding, from the data set, a logical block corresponding to the process parameter with the smallest one of the averages.

In various aspects and embodiments described herein, the steps of obtaining the result of the statistical data analysis, calculating the ratio of the correlation value to the confidence value, calculating the average of the absolute values of the ratios and excluding the values of the one of the process parameters are iterated until at least one specified condition is met. The "specified condition" may be, for example, a predetermined or predeterminable stopping condition for the iteration. For instance, in some exemplary embodiments, the at least one specified condition may include a condition that the data set includes the values of a single process parameter after performing the step of excluding the values of the one of the process parameters.

In various aspects and embodiments described herein, in some circumstances, the interpretability of the results of the statistical data analysis can increase as the number of process parameters in the data set can decrease. To remove non-significant process parameters without a clear metric nor strategy may be very difficult and cumbersome.

In some exemplary embodiments, the result of the statistical data analysis may include:
a model representing relationships between the process parameters and the at least one process output value; and
at least one quality measure of the model.

Further, the method may further comprise outputting the at least one quality measure of the model included in the result of the statistical data analysis obtained in each iteration of the steps of obtaining the result of the statistical data analysis, calculating the ratio of the correlation value to the confidence value, calculating the average of the absolute values of the ratios and excluding the values of the one of the process parameters.

Further, in the exemplary embodiments where the result of the statistical data analysis includes a model representing relationships between the process parameters and the at least one process output value, the correlation value for the values of each process parameter obtained at each group of corresponding time points during the plurality of batch processes may be obtained by calculating a correlation between:

the values of the process parameter obtained at the group of corresponding time points during the plurality of batch processes, and
at least one predicted process output value that is predicted using the model.

Further, the at least one specified condition may include a condition defined according to the at least one quality measure of the model.

In some exemplary embodiments, the statistical data analysis may be partial least squares (PLS) or orthogonal partial least squares (OPLS). Both PLS and OPLS may be understood as methods for relating two data matrices, X and Y, to each other by a linear multivariate model. In PLS and OPLS, the matrix X may be referred to as a "predictor matrix" and the matrix Y may be referred to as a "response matrix". In various aspects and embodiments described herein, the matrix X may include the values of the process parameters and the matrix Y may include the at least one process output value.

PLS may be used to find the fundamental relations between the two matrices, X and Y, in other words, a latent variable approach to modeling the covariance structures in these two spaces (see e.g., P. Geladi and B. R. Kowalski, "Partial least-squares regression: a tutorial," Anal. Chim. Acta, vol. 185, no. Supplement C, pp. 1-17, January 1986; and S. Wold, M. Sjöström, and L. Eriksson, "PLS-regression: a basic tool of chemometrics," Chemom. Intell. Lab. Syst., vol. 58, no. 2, pp. 109-130, October 2001). A PLS model can find a sub-space approximating the training data similar to principal component analysis (PCA) (S. Wold, K. Esbensen, and P. Geladi, "Principal component analysis," Chemom. Intell. Lab. Syst., vol. 2, no. 1, pp. 37-52, August 1987), which is used for predictions.

OPLS may be considered as a variant of PLS and can enable filtering out structured noise in the data set by modeling variations of the predictor matrix X into three parts: a predictive part correlated to the response matrix Y, an orthogonal part that is uncorrelated to the response matrix Y and a residual part that represents the variation that is not explained by the model.

In the exemplary embodiments where the statistical analysis is PLS or OPLS, the at least one quality measure of the model may include: an $R^2$ value indicating a goodness of fit and/or $Q^2$ value indicating a goodness of prediction.

According to various aspects and embodiments described herein, in some circumstances, the $Q^2$ value can increase with no or small decrease in $R^2$ as models are constructed with data sets with excluded process parameter(s).

Further, in the exemplary embodiments where the statistical analysis is PLS or OPLS, the values of each process parameter obtained at each group of corresponding time points during the plurality of batch processes may correspond to a variable of a predictor matrix X of PLS or OPLS. Further, in such exemplary embodiments, the correlation value may be:
a p-loading value of the corresponding variable of the predictor matrix X,
a value indicating a calculated correlation between scaled values of the corresponding variable of the predictor matrix X and X-scores T of OPLS,
a weight value of the corresponding variable of the predictor matrix X, used for obtaining the X-scores T from X-residuals E of PLS or OPLS,
a weight value of the corresponding variable of the predictor matrix X, used for obtaining the X-scores T from the variables of the predictor matrix X, a centered and scaled coefficient of the corresponding variable of the predictor matrix X, or a variable importance in projection, VIP, value of the corresponding variable of the predictor matrix X, the VIP value indicating an influence on the response matrix Y of the corresponding variable of the predictor matrix X.

In another aspect, a computer program product is provided. The computer program product comprises computer-readable instructions that, when loaded and run on a computer, cause the computer to perform the method according to any one of the above-stated aspect and exemplary embodiments.

In yet another aspect, a system is provided for analyzing data obtained with respect to a chemical and/or biological process. The system comprises:

a storage medium storing a data set including the data obtained with respect to the chemical and/or biological process, wherein:

the chemical and/or biological process is carried out in a plurality of batch processes having a finite duration, values of process parameters relating to the chemical and/or biological process are obtained at a plurality of time points during each batch process, each time point in one of the plurality of batch processes having corresponding time points in other ones of the plurality of batch processes, at least one process output value is obtained at or after an end of each batch process, the data set includes, for each batch process, the values of the process parameters and the at least one process output value; and a processor configured to:

obtain a result of statistical data analysis on the data set, the result of the statistical data analysis including, for the values of each process parameter obtained at each group of corresponding time points during the plurality of batch processes, a correlation value and a confidence value corresponding to a confidence interval of the correlation value, the correlation value indicating a correlation between:

the values of the process parameter obtained at the group of corresponding time points during the plurality of batch processes, and the at least one process output value;

calculate, for the values of each process parameter obtained at each group of corresponding time points during the plurality of batch processes, a ratio of the correlation value to the confidence value;

calculate, for each process parameter, an average of absolute values of the ratios calculated for the values of the process parameter obtained at different groups of the corresponding time points during the plurality of batch processes;

exclude, from the data set, the values of one of the process parameters having a smallest one of the averages calculated for the process parameters; and iterate, until at least one specified condition is met, the steps to obtain the result of the statistical data analysis, calculate the ratio of the correlation value to the confidence value, calculate the average of the absolute values of the ratios and exclude the values of the one of the process parameters.

In some exemplary embodiments, the at least one specified condition may include a condition that the data set includes the values of a single process parameter after performing the step of excluding the values of the one of the process parameters.

Further, in some exemplary embodiments, the result of the statistical data analysis may include:

a model representing relationships between the process parameters and the at least one process output value; and at least one quality measure of the model.

Further, the processor may be further configured to: output the at least one quality measure of the model included in the result of the statistical data analysis obtained in each iteration of the steps to obtain the result of the statistical data analysis, calculate the ratio of the correlation value to the confidence value, calculate the average of the absolute values of the ratios and exclude the values of the one of the process parameters.

Further, in the exemplary embodiments where the result of the statistical data analysis includes a model representing relationships between the process parameters and the at least one process output value, the correlation value for the values of each process parameter obtained at each group of corresponding time points during the plurality of batch processes may be obtained by calculating a correlation between:

the values of the process parameter obtained at the group of corresponding time points during the plurality of batch processes, and at least one predicted process output value that is predicted using the model.

Further, the at least one specified condition may include a condition defined according to the at least one quality measure of the model.

In some exemplary embodiments, the statistical data analysis may be partial least squares, PLS, or orthogonal partial least squares, OPLS. Further, the at least one quality measure of the model may include: an $R^2$ value indicating a goodness of fit and/or $Q^2$ value indicating a goodness of prediction.

Further, in some exemplary embodiments, the values of each process parameter obtained at each group of corresponding time points during the plurality of batch processes may correspond to a variable of a predictor matrix X of PLS or OPLS.

Further, the at least one process output value may correspond to at least one variable of a response matrix Y of PLS or OPLS. Moreover, the correlation value may be:

a p-loading value of the corresponding variable of the predictor matrix X, a value indicating a calculated correlation between scaled values of the corresponding variable of the predictor matrix X and X-scores T of OPLS, a weight value of the corresponding variable of the predictor matrix X, used for obtaining X-scores T from X-residuals E, a weight value of the corresponding variable of the predictor matrix X, used for obtaining X-scores T from the variables of the predictor matrix X, a centered and scaled coefficient of the corresponding variable of the predictor matrix X, or a variable importance in projection, VIP, value of the corresponding variable of the predictor matrix X, the VIP value indicating an influence on the response matrix Y of the corresponding variable of the predictor matrix X.

The subject matter described in the application can be implemented as a method or as a system, possibly in the form of one or more computer program products. The subject matter described in the application can be implemented in a data signal or on a machine readable medium, where the medium is embodied in one or more information carriers, such as a CD-ROM, a DVD-ROM, a semiconductor memory, or a hard disk. Such computer program products may cause a data processing apparatus to perform one or more operations described in the application.

In addition, subject matter described in the application can also be implemented as a system including a processor, and a memory coupled to the processor. The memory may encode one or more programs to cause the processor to perform one or more of the methods described in the application. In some examples, the system may be a general purpose computer system. In other examples, the system may be a special purpose computer system including an embedded system.

In some circumstances, any one of the above stated aspects as well as any one of various embodiments and examples described herein may facilitate analysis and/or control of the chemical and/or biological process. For example, a sparser model that can be created from the data set with data of one or more process parameters being removed may make it easier for the process expert to interpret what is causal information and what might be spurious correlations. Further, some hypothesis may be declined as the local blocks when that hypothesis is eliminated as non-significant.

Further, it is noted that the various aspects and embodiments described herein may be applied in various technical fields involving chemical and/or biological processes. Examples of the application fields of the various aspects and embodiments described herein may include, but are not limited to: chromatography; filtration; centrifugation; freeze drying; blending, granulation, drying, sieving and/or mixing for small molecule pharmaceuticals; synthesis, blending, mixing, and/or drying in chemistry; pulp and paper; food and beverages; clean-in-place (CIP) which is a method of automated cleaning the interior surfaces of pipes, vessels, equipment, filters and associated fittings, without major disassembly; steam-in-place (or sterilize-in-place, SIP) which is a timed sterilization of the upstream and downstream biopharmaceutical production train with clean steam; pressure test performed to ensure safety, reliability and leak tightness of a pressure system; etc.

BRIEF DESCRIPTION OF THE DRAWINGS

Details of one or more implementations are set forth in the exemplary drawings and description below. Other features will be apparent from the description, the drawings, and from the claims. It should be understood, however, that even though embodiments are separately described, single features of different embodiments may be combined to further embodiments.

FIG. 9 shows a list of ratios of correlation values to confidence values for the process parameters shown in FIG. 8 regarding the exemplary experiment.

DETAILED DESCRIPTION OF EMBODIMENTS

In the following text, a detailed description of examples will be given with reference to the drawings. It should be understood that various modifications to the examples may be made. In particular, one or more elements of one example may be combined and used in other examples to form new examples.

When modelling biological data, empirical models may be required since the theoretical foundation often excludes first principle models. For chemistry, although the theories are older and may be considered much stronger than those for biology, some chemical processes still involve many unknowns. Multivariate modeling methods have been developed, where the modeling starts from a large number of variables to visualize, monitor, forecast, control and predict selected quality parameters. For multivariate modeling methods, it may be required to obtain optimal results and visualize the results in an optimal and understandable manner to users and/or regulatory authorities.

For both chemistry and biology, there is a strive to move from batch data to continuous processes (also referred to as "steady state process") and this work has gone much further in chemistry. When enough is known on a system, a continuous process (in other words steady state process) may be preferred for, e.g. environmental and/or economic reasons. Thus, broadly speaking, batch processes may be considered as processes where less is known and variation is larger.

In chemical processes, defined molecules may react with each other. A practical problem may be that no chemical entity is 100% clean so there is almost always a small amount of other chemicals that can (and, in most cases, will) affect the chemical process and the result of the process.

In bioprocesses, there may be cells that accomplish the work. Development and/or production involving bioprocesses may thus often be based on one single clone. Even when one starts with a single clone, however, experiments and/or production may often be performed with a mixture between the starting clone and its siblings since mutation may happen in many cases.

Accordingly, chemical and/or biological processes may have large variations.

System Configuration

Figure 1:
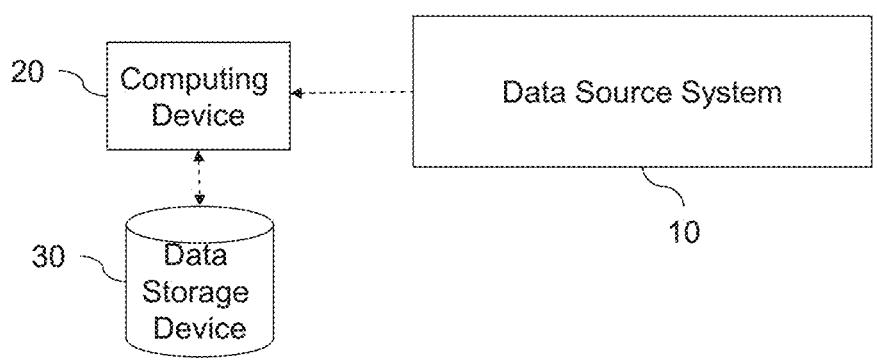
FIG. 1 shows a schematic diagram of an exemplary system for data analysis.

FIG. 1 shows a schematic diagram of an exemplary system for data analysis. The exemplary system shown in FIG. 1 comprises a data source system 10, a computing device 20 and a data storage device 30.

The data source system 10 may be a system that generates and/or collect data to be analyzed. Further, the data source device 10 may be configured to provide the computing device 20 with the data to be analyzed. For example, the data source system 10 may comprise a device (e.g., a computer) for collecting data with respect to an experiment and/or production involving a chemical and/or biological process. Further, the data source system 10 may include or be connected to a setup for carrying out the experiment and/or production. In some exemplary embodiments, the data source system 10 may comprise a bioreactor system in which cell culture processes may be carried out. For example, the bioreactor system comprised in the data source system 10 may be a multi-parallel bioreactor system that is configured to carry out a high throughput processes where large amounts of data (e.g., more than 200 process parameters for a chemical process, more than 50 process parameters for a biological process and more than 20 process outputs) may be generated.

The data to be analyzed, which may be collected by the data source system 10, may include values of process parameters relating to a chemical and/or biological process and at least one process output value of the chemical and/or biological process. Details of the data will be described later below with reference to FIG. 2.

Referring to FIG. 1, the computing device 20 may be a computer connected to the data source system 10 via (a) wired and/or wireless communication network(s). The computing device 20 may obtain data to be analyzed from the data source system 10. Further, the computing device 20 may be configured to obtain a result of statistical data analysis on a data set including the data that is obtained with respect to the chemical and/or biological process, collected by the data source system 10. In some circumstances, the computing device 20 may perform the statistical data analysis on the data set to obtain the result. In other circumstances, the statistical data analysis may be performed on the data set by the data source system 10 or any other device separate from the computing device 20 and the computing device 20 may receive the result from the data source system 10 or the other device. The computing device 20 may be configured to perform a method according to various embodiments and examples described herein. The data storage device 30 may store information that is used by the computing device 20 and/or information that is generated by the computing device 20.

It is noted that the data source system 10, the computing device 20 and the data storage device 30 may either be incorporated into a single device with one body or implemented with more than one separate devices. Further, the computing device 20 may be implemented with more than one computer connected to each other via (a) wired and/or wireless communication network(s).

Data Structures—Batch Evolution Model and Batch Level Model

The data obtained and analyzed in the exemplary system shown in FIG. 1 may be obtained with batch processes rather than continuous processes. In contrast to a continuous process, a batch process has a finite duration, from initialization to completion.

Figure 2:
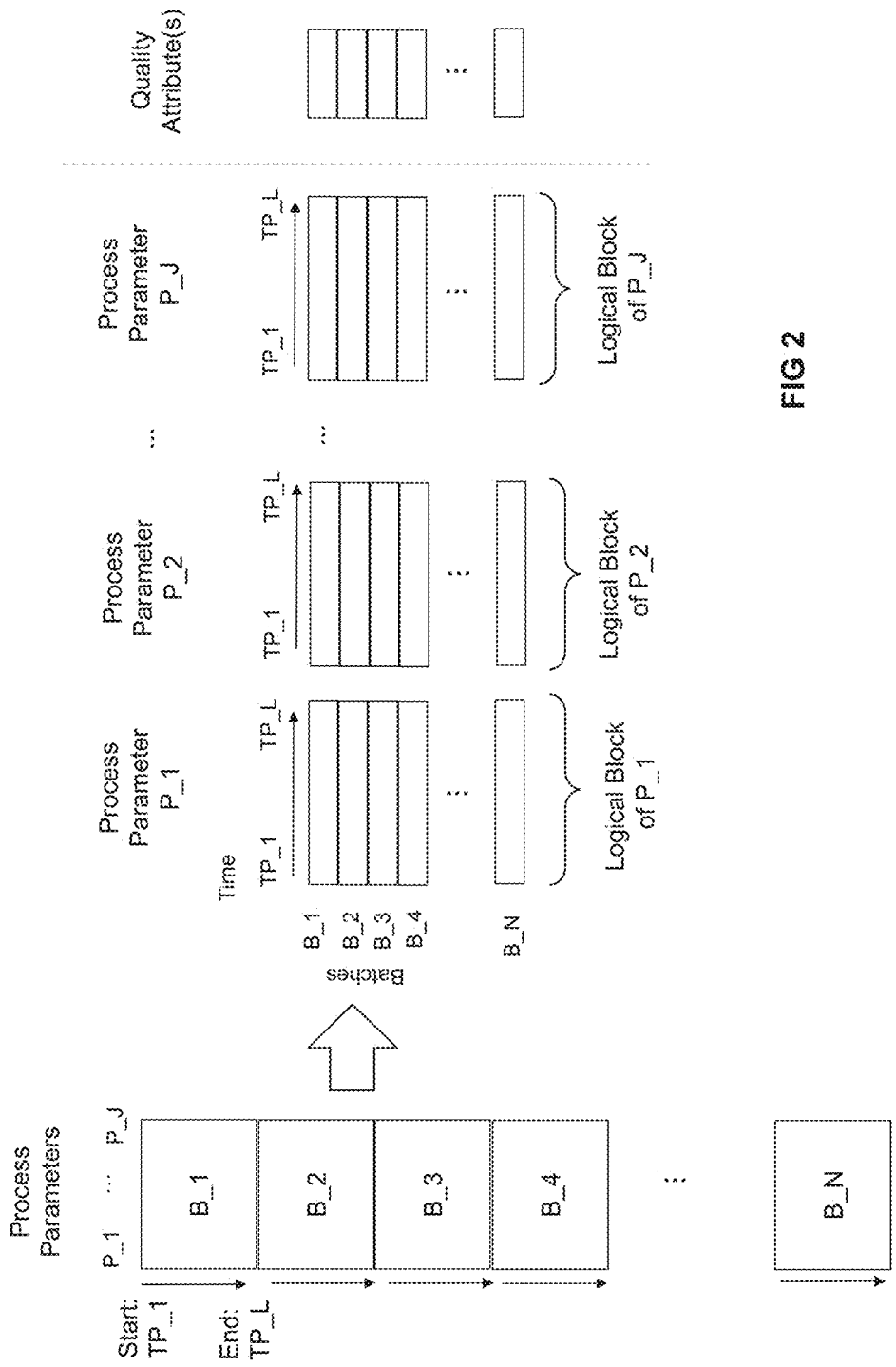
FIG. 2 shows a schematic diagram representing data structures of data that may be obtained with respect to a chemical and/or biological process.

FIG. 2 shows exemplary data structures of data obtained with batch processes. As also stated above and as indicated in FIG. 2, each batch process has a finite duration, from a start to an end. During each of the batch processes B_1, B_2, . . . , B_N, values of a plurality of process parameters P_1, P_2, . . . , P_J may be obtained (e.g., measured or derived from one or more measurement(s)) at a plurality of time points TP_1, TP_2, . . . , TP_L during the batch process (note that N, J and L are integer numbers larger than 1). The plurality of time points TP_1, TP_2, . . . , TP_L may occur in a specified time interval, e.g., every 10 minutes, every hour, every day, every other day, etc. Further, each batch process may provide one or more process output values that may be considered as one or more (critical) quality attributes.

It is noted that the time points TP_1, TP_2, . . . , TP_L in the plurality of batch processes B_1, B_2, . . . , B_N may be grouped into groups of corresponding timing at which the time points occur. Thus, for example, the l-th time point (l=1, 2, . . . , L) in each of the plurality of batch processes B_1, B_2, . . . , B_N may be considered as belonging to a same group of corresponding time points.

FIG. 2 shows two exemplary data structures: batch evolution model and batch level model.

In the batch evolution model, shown on the left hand side of FIG. 2, the data from the batch processes B_1, . . . , B_N may be arranged in a matrix with columns corresponding to the process parameters P_1, P_J and rows corresponding to time points TP_1, . . . , TP_L within batch processes B_1, . . . , B_N. Usually, trajectories of the process parameters in batch processes may describe dynamic time dependencies, in other words, the numerical values of the process parameters may change as a result of batch progress. Further, these numerical values may change differently during batch evolution. In addition to varying operating conditions within each batch, batch processes may generally exhibit moderate to large batch-to-batch variation. Such between-batch variations may arise because of deviations of the process parameters from their target trajectories, errors in the charging and initialization of batches, and/or fluctuations linked to variation in starting materials and their impurity profiles.

Visualization according to the batch evolution model may be very effective for monitoring, forecasting and control of the batch-to-batch variation.

In the batch level model, shown on the right hand side of FIG. 2, the data from the batch processes B_1, . . . , B_N may be arranged in a matrix with rows corresponding to batch processes B_1, . . . , B_N and each column corresponding to one of the time points TP_1, . . . , TP_L for one of the process parameters P_1, . . . , P_J. More specifically, for constructing a matrix according to the batch level model, values of the process parameters P_1, . . . , P_J may be divided in segments corresponding to the batch process B_1, . . . , B_N. The segmented values of the process parameters P_1, . . . , P_J may then be re-ordered such that the values of the process parameters P_1, . . . , P_J form one row vector, where in each row, values of the first process parameter P_1 obtained in the corresponding batch process is ordered by time and are followed by values of the second process parameter P_2 obtained in the same corresponding batch process ordered by time, followed further by values of the third process parameter P_3 obtained in the same corresponding batch process ordered by time, and so on. Accordingly, each column of the matrix according to the batch level model shown in FIG. 2 may comprise values of one of the process parameters P_1, . . . , P_J obtained at a corresponding group of time points TP_1, TP_2, . . . , TP_L. In other words, the variables of the batch level model may be scores, original variables, or summary variables (statistics of the original variables) of the batch evolution model at every time point unfolded sidewise.

The matrix according to the batch level model shown in FIG. 2 may contain as many rows as the number of batch processes for the data set (e.g., training data set) and therefore can be used to predict the quality attribute(s).

Further, in the present disclosure, a group of values of a same process parameter P_1, P_2, ..., or P_L obtained at the time points TP_1, TP_2, ..., TP_L during the batch processes B_1, B_2, ..., B_N may be considered as a "logical block" corresponding to that process parameter, as shown in FIG. 2.

The re-arrangement of the batch evolution model to the batch level model may be necessary in order to establish control charts for monitoring the development of new batches, as well as to be able to predict quality attributes. Batch level models may be commonly applied to investigate variations between batches, sites, campaigns and/or to study impact of process variations on product quality.

Exemplary Types of Data

In some exemplary embodiments, the data source system 10 in the exemplary system shown in FIG. 1 may collect the following three types of data from a chemical and/or biological process (e.g., each batch process):

In-line and online data may be obtained without removing a sample from a reactor in which the process is carried out. Examples of the in-line and online data may include, but are not limited to, temperature, agitation, pressure, pH, flow of air, $CO_2$, oxygen, etc. Some parameters of in-line and online data such as the temperature and agitation may be measured accurately. Values of some parameters measured with a certain kind of sensors such as pH sensors may drift over time and may require adjustments. Values of some parameters such as flow of air, $CO_2$, oxygen may include more noise. The process parameters as mentioned above may include parameters of the in-line and online data.

At-line data may be obtained by removing a sample from the reactor and measuring the value with some type of device. For example, at-line data may include an amount of a particular substance (e.g., glucose, glutamate, sodium, potassium, etc.) in the sample removed from the reactor. The process parameters as mentioned above may include parameters of the at-line data. The at-line data can be the most valuable data for analyzing and/or controlling the process. Obtaining the at-line data in a reliable manner, however, may be difficult in some circumstances. For example, one or more of the following factors may need to be considered: assuring that the samples are collected at regular time intervals, assuring that the sample is representative for the whole process, assuring that the sample to degrade from between sampling and measurement, cleaning of the sample so that the measurement can be done, accuracy of the measurement method.

Process output data may be obtained (e.g., measured or derived from one or more measurements) at or after the end of the process and may be related to quality and/or economy of the process. The process output value as mentioned above may be a value of a parameter of the process output data. Examples of the process output data may include, but are not limited to, yield (e.g., in a chemical process), titer (e.g., in a bioprocess) and an amount of by-product. The yield in a chemical process may be a very important parameter and may often be measured accurately. The titer in a bioprocess may also be measured relatively accurately. Since the amount of by-product may be down to per mille levels or, in some circumstances, down to ppm levels, accuracy of the measurement may be lower than that for the yield and titer.

Since different parameters of the obtained data may have different levels of measurement accuracy as stated above, the variation from the process may be enhanced when considering the measured data.

Exemplary Methods of Statistical Data Analysis

As stated above with reference to FIG. 1, the computing device 20 may obtain a result of statistical data analysis on a data set including data that is obtained with respect to a chemical and/or biological process, collected by the data source system 10. A method of the statistical data analysis may be a multivariate modeling method with which a model of the chemical and/or biological process is constructed from the data set including data of a plurality of variables. The following provides two exemplary methods of the statistical data analysis, partial least squares (PLS) and orthogonal partial least squares (OPLS), which may be used by the computing device 20.

Partial Least Squares (PLS)

PLS regression is a widely used regression model within, for example, chemometrics and related areas. Given a predictor matrix (e.g., a training data matrix) X with N rows of observations and K columns of variables, with a corresponding response matrix (e.g., a target matrix) Y with N rows of observations and M columns of responses, a PLS model may summarize both data-matrices. When applied in the various embodiments and examples described herein, N, K and M are all integers, where N, K>1 and M>0. Further, when applied in the various embodiments and examples described herein, the predictor matrix X may be a matrix of data in the batch level model described above with reference to FIG. 2. Accordingly, for example, the K columns of variables in the predictor matrix X may correspond to the time points TP_1, ..., TP_L for each of the process parameters P_1, ..., P_J and, thus, K=L×J. Further, the rows of the predictor matrix X may correspond to the plurality of batch processes B_1, ..., B_N. In addition, the response matrix Y may correspond to a matrix of the quality attribute(s) shown in FIG. 2. Thus, the rows of the response matrix Y may correspond to the plurality of batch processes B_1, ..., B_N and the column(s) of the response matrix Y may correspond to one or more quality attributes, e.g., one or more parameters for the process output value(s).

Similar to the principal component analysis (PCA) where principal components that represent uncorrelated, reduced dimensions of a data set, PLS may find full-rank sub-spaces, of a dimension A, called "latent variable spaces" that approximate the matrices X and Y. In contrast to the PCA, PLS may maximize the covariance between the sub-spaces found, instead of maximizing the variance of a single sub-space. In short, PLS may approximate the input data as:

$$X = TP' + E \tag{1}$$

Where $T = [t_1, \ldots, t_A]$ may be an N×A latent variable matrix, called a score matrix, spanning a full-rank sub-space of the column-space of the predictor matrix X and maximizing the covariance with the response matrix Y, P may be K×A matrix of PLS loadings, and E may be an N×K matrix of approximation residuals. The loadings may contain the linear combination weights used to approximate the predictor matrix X from the score matrix T. The response matrix Y may be approximated in a similar way. More details on how to calculate the PLS model and use it for regression can be found in S. Wold, M. Sjöström, and L. Eriksson, "PLS-regression: a basic tool of chemometrics," Chemom. Intell. Lab. Syst., vol. 58, no. 2, pp. 109-130, October 2001.

Orthogonal Partial Least Squares (OPLS)

OPLS may be considered as a variant of PLS and can enable filtering out structured noise in the data set by modeling variations of the predictor matrix X into three parts: a predictive part correlated to the response matrix Y, an orthogonal part that is uncorrelated to the response matrix Y and a residual part that represents noise. The predictor matrix X may be a N×K matrix and the response matrix Y may be a N×M matrix as described above with regards to PLS. Accordingly, when applied in the various embodiments and examples described herein, the rows of the predictor matrix X and the response matrix Y may correspond to the plurality of batch processes B_1, . . . , B_N, the columns of the predictor matrix X may correspond to the time points TP_1, . . . , TP_L for the process parameters P_1, . . . , P_J and the columns of the response matrix Y may correspond to one or more quality attributes (see also, e.g., FIG. 2).

In case of a single response variable (in other words, the number M of the columns in the response matrix Y is one), the X-part of the OPLS model may be expressed as follows:

$$X = 1\bar{x}' + tp' + ToPo' + E \qquad (2)$$

where:

$\bar{x}'$ may be a vector of the predictor variables, centered and scaled to unit variance, t may be a vector including scores of predictive components of the predictor matrix X, p' may be a vector including loadings of predictive components of the predictor matrix X, To may be an N×(A−1) matrix including scores of orthogonal components of the predictor matrix X, A being the number of components in the model, Po may be a K×(A−1) matrix including loadings of orthogonal component of the predictor matrix X, and E may be an N×K matrix of residuals.

Further, the OPLS model prediction of single y (e.g., in case M=1 for the response matrix Y) may be expressed as follows:

$$y = \bar{y}' + uq' + F \qquad (3)$$

where:

$\bar{y}'$ may be a vector of the response values, centered and scaled to unit variance, u may be a vector including scores of the response matrix Y (in the case of M=1, the response vector y), q may be a vector including loadings of the response matrix Y (in the case of M=1, the response vector y), and F may be an N×M matrix of residuals.

Figure 3:
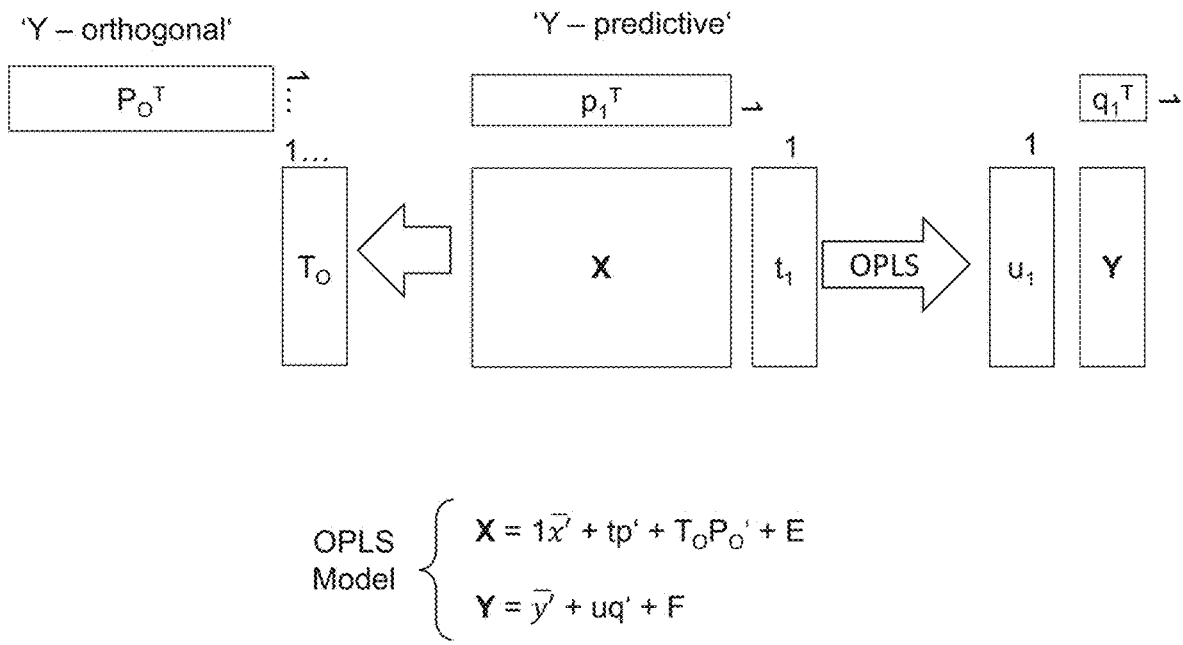
FIG. 3 shows a schematic diagram for explaining an OPLS model.

FIG. 3 shows a schematic diagram representing the OPLS model as described above.

Figure 4:
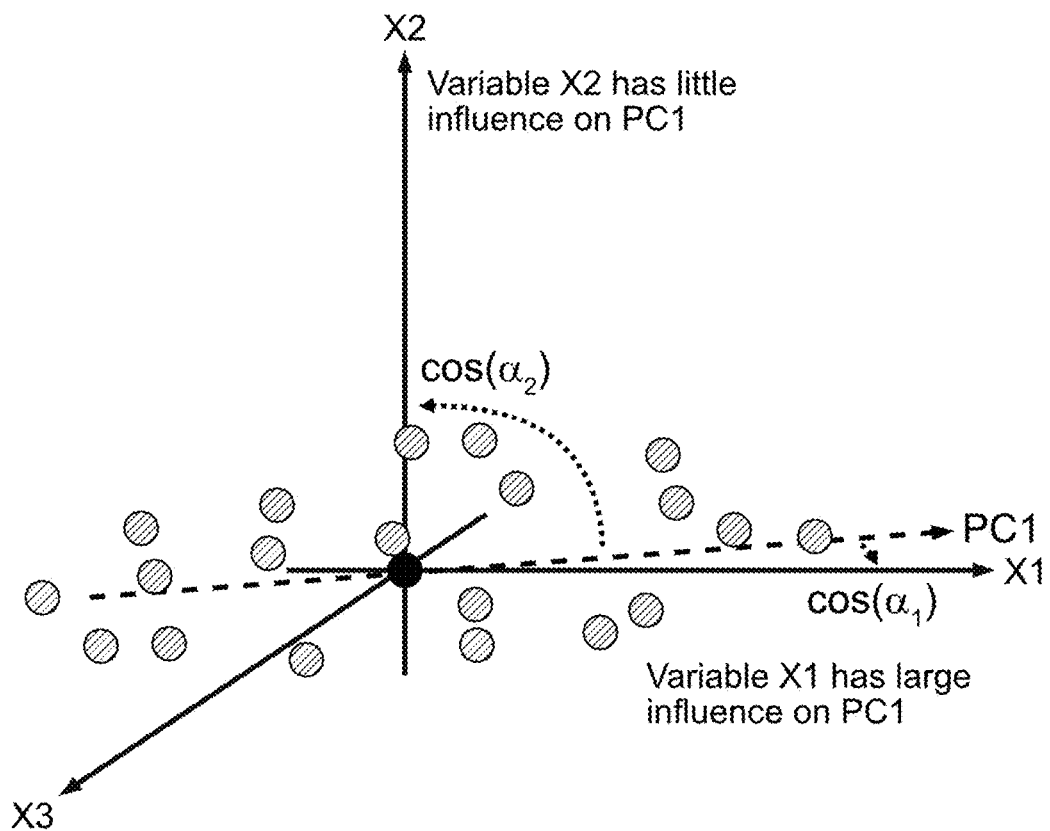
FIG. 4 shows a schematic diagram for explaining a concept of loading values in OPLS.

Algebraically, the loadings p may inform how the K variables (corresponding to the K columns) of the predictor matrix X are linearly combined to form the scores T. The loadings p may unravel the magnitude, (e.g., large or small correlation) and the manner (e.g., positive or negative correlation) in which the measured variables in the predictor matrix X contribute to the scores T. For each principal component of the OPLS model, every variable $x_k$ (k=1, . . . , K) in the predictor matrix X may have a loading value assigned. For example, as shown in FIG. 4, the loading of a variable $x_k$ may depend on its angle α relative to the principal component. The loading value may have a maximum range from −1 to 1. Accordingly, the loading value calculated from cos(a) may be the following: cos(0°)=1; cos(90°)=0; cos(180°)=−1; cos(270°)=0.

Quality Measures for a PLS or OPLS Model

Prediction may be the model fit that may tell how well the responses, Y variable data, of the training data set can be mathematically reproduced. The predictive ability may be how reliably the outcome of future processes can be predicted as estimated by cross validation.

A quantitative measure of the goodness of fit may be given by a parameter $R^2$ (e.g., the explained variation) of the Y variable. The predictive ability, on the other hand, may be given by the goodness of prediction parameter $Q^2$ (e.g., the predicted variation) of the Y-variable.

More specifically, $R^2$ may reflect the amount of described variation:

$$R^2 = 1 - RSS/SSX,$$

where SSX may be a sum of squares of X variables (in other words, total variation of the predictor matrix X), and $$RSS = \Sigma(observed - predicted)^2.$$

The "observed" values may be the historical actual values (e.g., actually obtained during and/or after the chemical and/or biological process) and the "predicted" values are the values predicted from the model.

Further, $Q^2$ may be considered as a measure of the predictive ability of the model and may be expressed as:

$$Q^2 = 1 - PRESS/SSX,$$

where SSX may be a sum of squares of X variables and $$PRESS = \Sigma(observed - predicted\ via\ cross\ validation)^2.$$

Exemplary Process Flow

Figure 5:
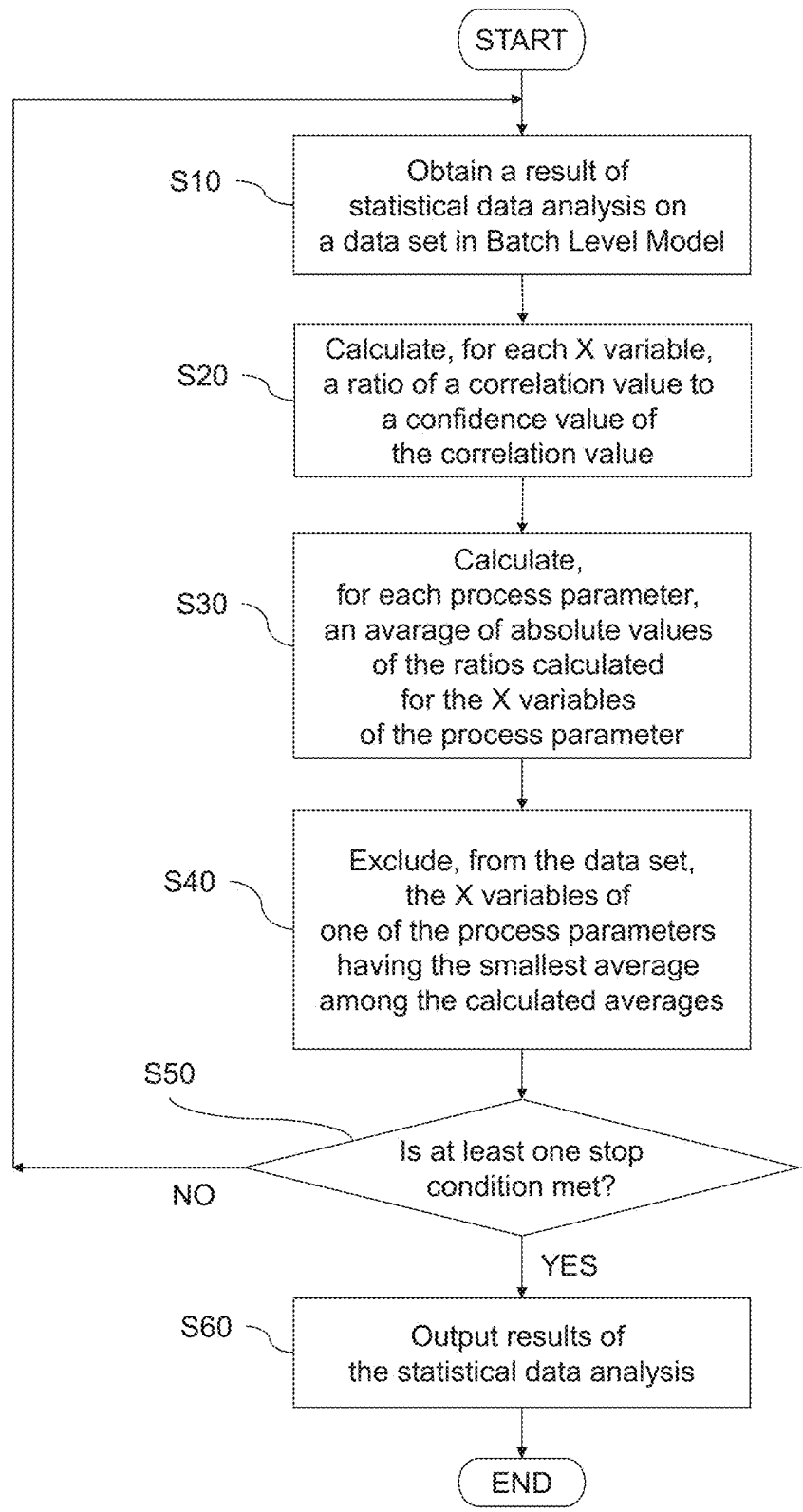
FIG. 5 shows a flowchart of an exemplary process performed by the exemplary system shown in FIG. 1.

FIG. 5 shows a flowchart of an exemplary process performed by the exemplary system shown in FIG. 1. The exemplary process of FIG. 5 may be performed by the computing device 20 shown in FIG. 1. The exemplary process may start, for example, when the computing device 20 receives, via an input device (not shown), an instruction from a user to start the exemplary process.

In step S10, the computing device 20 may obtain a result of statistical data analysis on a data set in batch level model. The data set may include data that is obtained, by the data source system 10, with respect to a chemical and/or biological process. As described above with reference to FIG. 2, the chemical and/or biological process may be carried out in a plurality of batch processes B_1, . . . , B_M having a finite duration. Further, the data set may include, for each batch process, values of the process parameters obtained at a plurality of time points TP_1, . . . , TP_L during the batch process, and at least one process output value (e.g., critical quality attribute) obtained at or after an end of the batch process. The values of the process parameters included in the data set may be arranged in a form of a matrix of the batch level model as shown in FIG. 2.

Referring again to FIG. 5, the computing device 20 may obtain the result of the statistical data analysis either by performing the statistical data analysis on the data set at the computing device 20 or by receiving the result from another device, e.g. the data source system 10. The result of the statistical data analysis may include, for the values of each process parameter obtained at each group of corresponding time points (e.g., TP_1, TP_2, . . . , or TP_L) during the plurality of batch processes B_1, . . . , B_N, a correlation value and a confidence value corresponding to a confidence interval of the correlation value. The correlation value may indicate a correlation between the values of the process parameter obtained at the group of corresponding time points during the plurality of batch processes and the at least one process output value. In some examples, the correlation value may be obtained by calculating a correlation between the values of the process parameter obtained at the group of corresponding time points during the plurality of batch processes and at least one predicted process output value that is predicted using a model included in the result of the statistical data analysis, the model representing relationships between the process parameters and the at least one process output value.

Further, in some exemplary embodiments, the result of the statistical data analysis may further include a model representing relationships between the process parameters and the at least on process output value. The result of the statistical data analysis may further include at least one quality measure of the model.

In some exemplary embodiments, the statistical data analysis in step S10 may be PLS or OPLS. In such exemplary embodiments, the predictor matrix X of PLS or OPLS may contain the values of the process parameters, with N rows of the matrix X corresponding to the batch processes B_1, . . . , B_N and with K columns of the matrix X corresponding to the time points TP_1, . . . , TP_L for each of the process parameters P_1, . . . , P_J and, thus, K=L×J (see also, FIG. 2, batch level model). The response matrix Y of PLS or OPLS may contain the at least one value for each batch process, with N rows of the matrix Y corresponding to the batch processes B_1, . . . , B_N and with M columns of the matrix Y corresponding to one or more quality attributes.

In the exemplary embodiments where OPLS is used as the statistical data analysis method in step S10, the value of the p-loadings (see e.g., equations (1) and (2)) for each X variable (e.g., a column in the predictor matrix X, the column corresponding to a combination of a process parameter and a time point) may be considered as the correlation value, as mentioned above, for the values of a process parameter obtained at a group of corresponding time points during the plurality of batch processes. The confidence value as mentioned above may thus be a value corresponding to the confidence interval of the p-loadings value. In some examples, the confidence value may be a standard error of the p-loadings value for the corresponding X variable. The standard error may be, for example, a jack-knife standard error of the p-loading computed from all rounds of cross validation.

Figure 6:
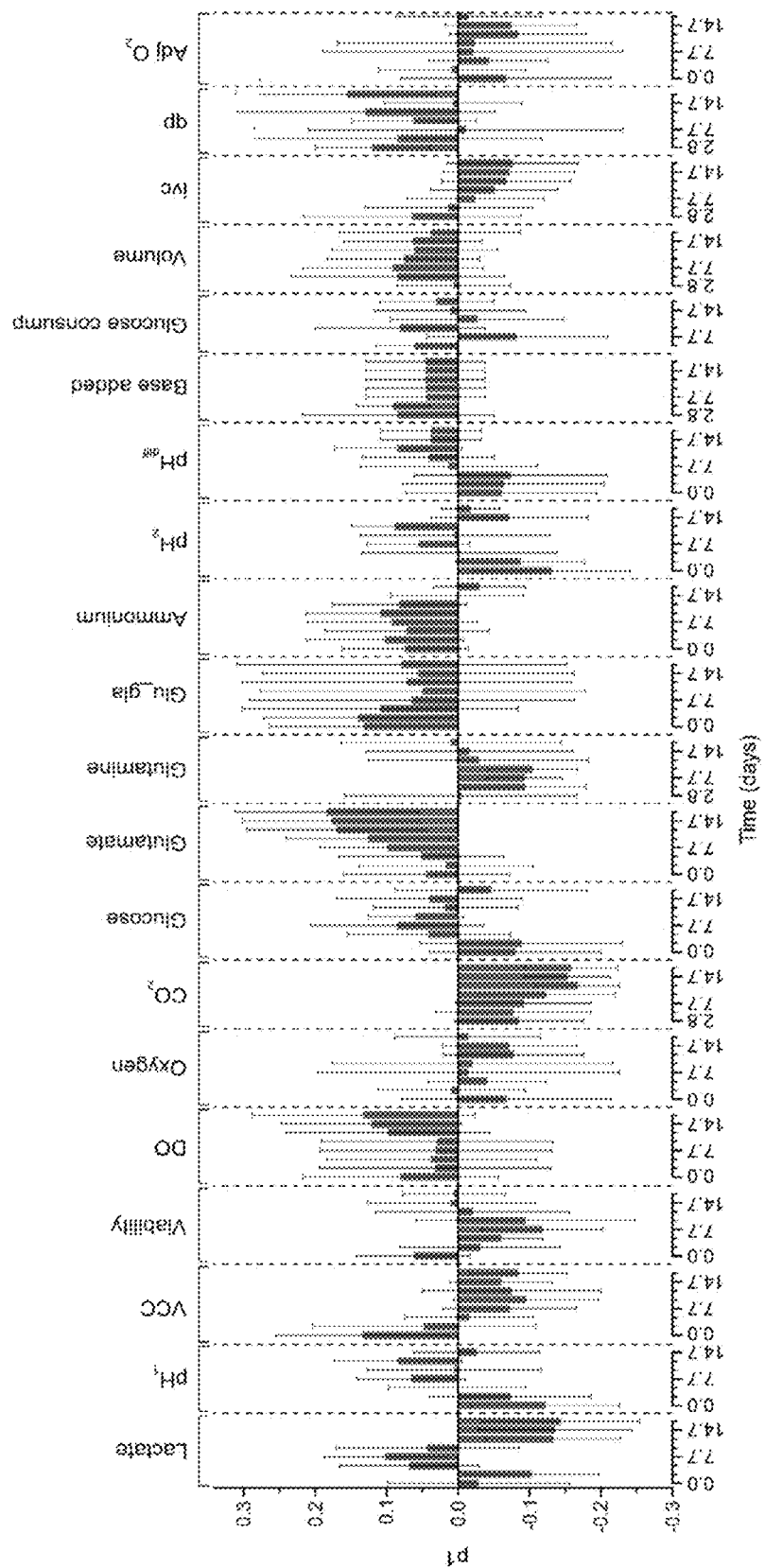
FIG. 6 shows an exemplary plot of p-loadings of process parameters in an OPLS model constructed with data obtained during an exemplary experiment.

FIG. 6 shows an error bar chart representing an example of the p-loadings for X variables and the standard errors of the p-loadings. The p-loadings and the standard errors shown in FIG. 6 may be included in the result of OPLS analysis on an exemplary data set obtained in an exemplary experiment. In the exemplary experiment, values of 20 process parameters were obtained (e.g., measured) at L=8 time points during each of N=24 batch processes. The obtained values were arranged as a matrix of the batch level model and that matrix was used as the predictor matrix X in the OPLS analysis. In FIG. 6, each rectangular bar and error bar represent the p-loading value and its standard error calculated for an X variable of the predictor matrix X. Each X variable corresponds to values of a process parameter obtained in a group of corresponding time points during the plurality of batch processes. Further, in FIG. 6, the X variables of 20 process parameters, in other words, 20 logical blocks, are shown and the X variables of a same process parameter or logical block are arranged next to each other. It is noted that the logical blocks are separated by broken lines in FIG. 6.

Referring again to FIG. 5, in the exemplary embodiments where the statistical data analysis method in step S10 is PLS or OPLS, the $R^2$ value and the $Q^2$ value as mentioned above may also be included in the result of the statistical data analysis as quality measures of the PLS or OPLS model.

After step S10, the exemplary process may proceed to step S20.

In step S20, the computing device 20 may calculate, for the values of each process parameter obtained at each group of corresponding time points during the plurality of batch processes, a ratio of the correlation value to the confidence value. For example, in case PLS or OPLS is performed on the data set as in the exemplary embodiments as stated above, a ratio of the p-loading value to the standard error of the p-loading value for each X variable may be calculated in step S20. After step S20, the exemplary process may proceed to step S30.

In step S30, the computing device 20 may calculate, for each process parameter, an average of absolute values of the ratios calculated for the values of the process parameter obtained at different groups of the corresponding time points during the plurality of batch processes. In other words, an average of absolute values of the ratios calculated for each logical block (see also, e.g., FIG. 2) may be calculated in step S30. For example, in the exemplary embodiments where PLS or OPLS is used as the statistical data analysis, an average of absolute values of the ratios of the p-loading values to the standard errors of the p-loading values for the X variables of the same process parameter (e.g., belonging to the same logical block) may be calculated. After step S30, the exemplary process may proceed to step S40.

In step S40, the computing device 20 may exclude, from the data set, the values of one of the process parameters having a smallest one of the averages calculated for the process parameters. In other words, the values in a logical block corresponding to the process parameter with the smallest average among the calculated averages may be excluded from the data set. For example, in the exemplary embodiments where PLS or OPLS is used as the statistical data analysis, the X variables of one of the process parameters (e.g., X variables belonging to one of the logical blocks) having the smallest average among the calculated averages may be excluded from the data set. After step S40, the exemplary process may proceed to step S50.

In step S50, the computing device 20 may determine whether at least one stop condition is met. The at least one stop condition may be one or more specified (e.g., predetermined or predeterminable) conditions. In some exemplary embodiments, the at least one stop condition may include a condition that the data set includes the values of a single process parameter after the exclusion step S40. In other words, the at least one stop condition may be met if the data set includes only values belonging to a single logical block after the exclusion step S40.

In some exemplary embodiments, the at least one stop condition used in step S50 may include a condition defined according to at least one quality measure of a model constructed with the statistical data analysis from the data set. In case the statistical data analysis is PLS or OPLS, the at least one quality measure may include the $R^2$ value indicating goodness of fit and/or the $Q^2$ value indicating goodness of prediction as described above.

In case the at least one stop condition is determined to be not met (NO in step S50), the exemplary process may return to step S10 and the steps S10 to S50 may be iterated. For example, in the exemplary embodiments where the at least one stop condition is a condition that values of only a single logical block (e.g., a single process parameter) is left in the data set, the stop condition is determined to be not met in case the data set still includes more than one logical block.

When the exemplary process returns to step S10 as a result of the determination in step S50, the statistical data analysis of step S10 may be performed on the data set without the values of the logical block excluded in step S40. For example, the computing device 20 may perform the statistical data analysis on the data set without the values of the excluded logical block to obtain a result of the statistical data analysis in step S10. In the statistical data analysis performed in step S10 for the second and subsequent iterations, one or more conditions of the statistical data analysis are preferably set identical to those in the first iteration. For example, in case the statistical data analysis in step S10 is PLS or OPLS, the same number A (=1, 2, . . . ) of components is preferably employed for the first iteration and the subsequent iterations.

In case the at least one stop condition is determined to be met (YES in step S50), the exemplary process may proceed to step S60.

In step S60, the computing device 20 may output results of the statistical data analysis obtained by the iterations of steps S10 to S50. For example, the computing device 20 may output the at least one quality measure of the model included in the result of the statistical data analysis obtained in each iteration of the steps S10 to S50. The computing device 20 may also output information indicating (values of) which of the plurality of process parameters were included in the data set subject to the statistical data analysis in each iteration of the steps S10 to S50. From the results output in step S60, the user may select a model including the process parameters that seem to be most relevant to the process output value(s) and use the selected model for further analysis and/or control of the chemical and/or biological process, for example. The exemplary process may end after step S60.

Figures 7A, 7B:
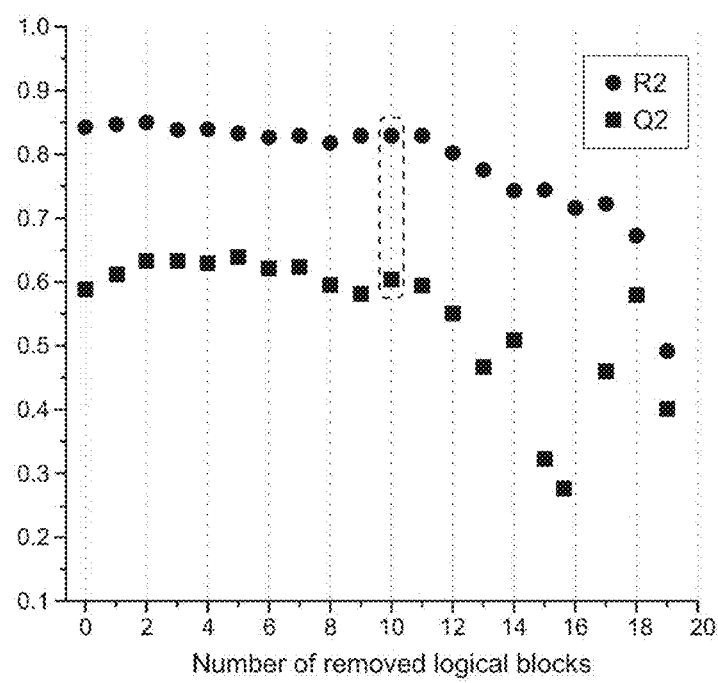
FIG. 7A shows an exemplary list of output results including quality measures, obtained by performing the exemplary process shown in FIG. 5 on the data obtained during the exemplary experiment.
FIG. 7B shows an exemplary plot of the output results shown in FIG. 7A.

FIGS. 7A and 7B show examples of the results of the statistical data analysis that may be output in step S60. More specifically, the results shown in FIGS. 7A and 7B are results of performing the exemplary process shown in FIG. 5 on the data set obtained in the exemplary experiment described above with reference to FIG. 6. In this specific example, the steps S10 to S50 of FIG. 5 were iterated until the data set included data of a single process parameter. Since the initial data set included 20 process parameters in this specific example and data of one process parameter (logical block) was removed from the data set in each iteration of steps S10 to S50, 20 iterations of steps S10 to S50 were performed. FIG. 7A shows a table that contains the $R^2$ value and the $Q^2$ value of each OPLS model constructed with OPLS analysis in step S10 during each iteration of the steps S10 to S50. The left column of the table shown in FIG. 7A represents the numbers of logical blocks (e.g., process parameters) removed from the data set. The middle and right columns of the table shown in FIG. 7A respectively represent the $R^2$ values (indicating goodness of fit) and $Q^2$ values (indicating goodness of prediction) of the models resulting from the OPLS analysis on the data set with the corresponding numbers of logical blocks being removed. FIG. 7B shows a graph including plots of the $R^2$ values and $Q^2$ values with respect to the numbers of removed logical blocks as shown in the table of FIG. 7A.

From the results shown in FIGS. 7A and 7B, it can be seen that the model with 10 logical blocks being removed has a combination of relatively high $R^2$ value and $Q^2$ value. The user may thus select the model with 10 logical blocks being removed for further analysis and/or control of the process of the exemplary experiment. Since the selected model includes fewer logical blocks (more specifically, 10 process parameters) as compared to the initial model without any removed logical block (see e.g., FIG. 6 with 20 process parameters), the selected model may facilitate further analysis and/or control of the process of the exemplary experiment.

Figure 8:
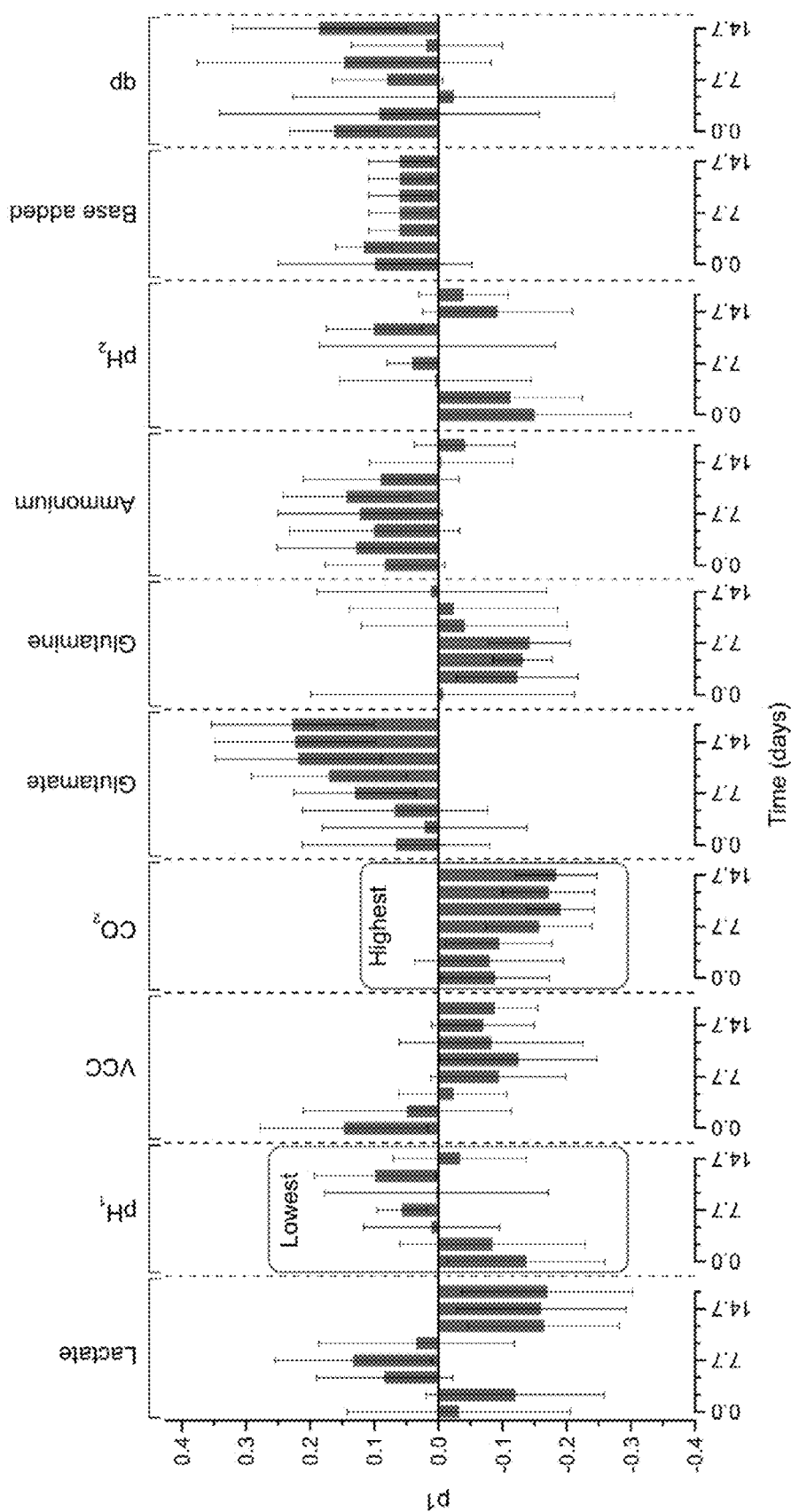
FIG. 8 shows an exemplary plot of loadings of process parameters in an OPLS model that is obtained by performing the exemplary process shown in FIG. 5 on the data obtained during the exemplary experiment.

FIG. 8 shows an error bar chart of the p-loadings for the X variables of the selected model with 10 logical blocks being removed as mentioned above with reference to FIGS. 7A and 7B. In FIG. 8, the p-loadings and the confidence values are shown in a manner analogous to that in FIG. 6. FIG. 8 shows the p-loadings and the confidence values of for 10 logical blocks included in the selected model after excluding 10 logical blocks from the initial model with 20 logical blocks as shown in FIG. 6. Additionally, FIG. 8 includes indications of the logical blocks having the highest and lowest averages of the absolute values of the ratios of the p-loadings to the confidence values. More specifically, in FIG. 8, the process parameter "$CO_2$" has the highest average of the absolute ratios and the process parameter "$pH_1$" has the lowest average of the absolute ratios.

Further, FIG. 9 shows averages of absolute values of the ratios of the p-loadings to the confidence values (e.g., standard errors) calculated for the 10 process parameters included in the selected model, in a descending order. As also mentioned above with reference to FIG. 8, the process parameter "$CO_2$" has the highest average and the process parameter "$pH_1$" has the lowest average.

Figure 10A:
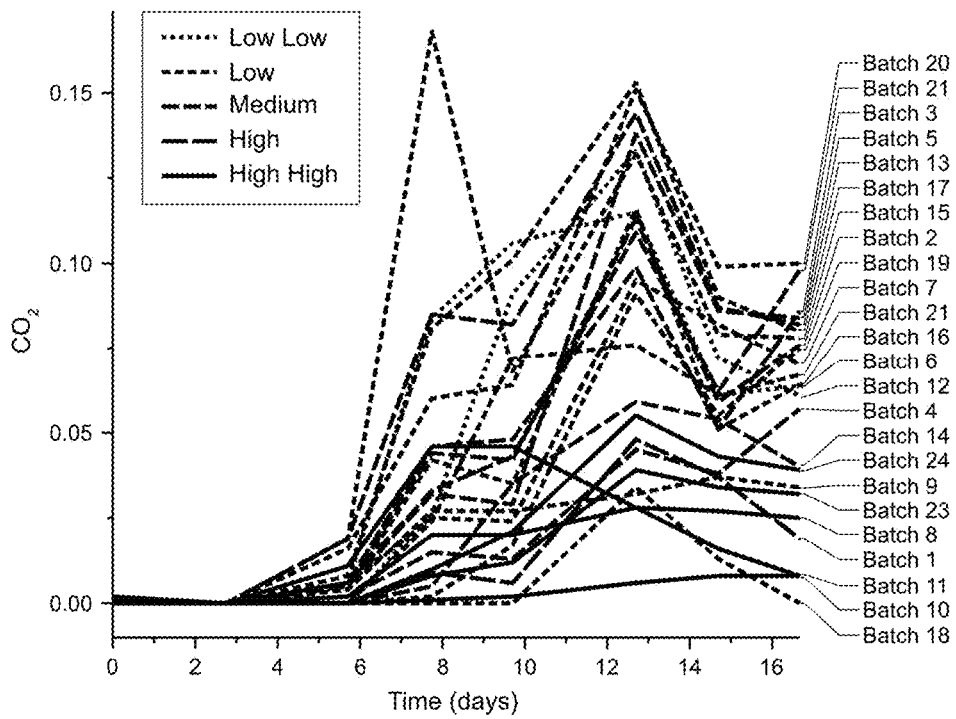
FIGS. 10A and 10B show exemplary plots of process parameter values measured during the exemplary experiment.
Figure 10B:
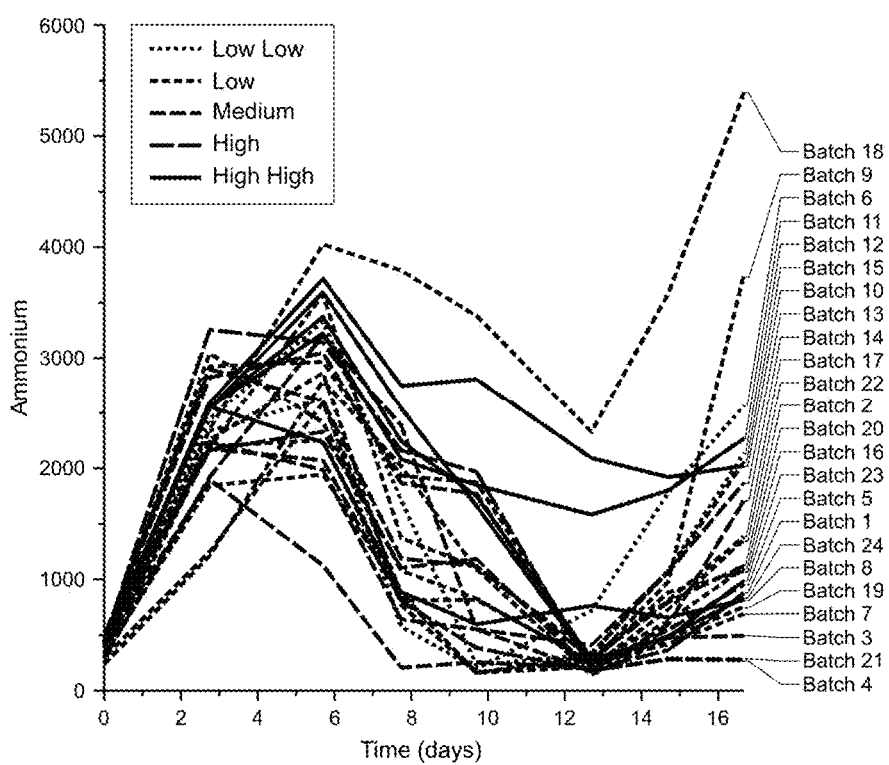

FIGS. 10A and 10B show plots of values of the process parameters "$CO_2$" and "ammonium", respectively, obtained in the exemplary experiment described above with reference to FIG. 6. FIGS. 10A and 10B show plots for the process parameters having relatively high averages of the ratios of the p-loadings to the confidence values. The plot shown in FIG. 10A of the process parameter "$CO_2$" demonstrates that the majority of the High-High Batches are the lower part of the plot while the majority of the Low-Low batches are at the top of the plot. Based on this data the p1 loading from OPLS will have a negative values as shown FIG. 6. The plot shown in FIG. 10B of the process parameter "ammonium" demonstrates that the majority of the High-High Batches are the higher part of the plot while the majority of the Low-Low batches are at the bottom of the plot. Based on this data the p1 loading from OPLS will have a positive values as shown FIG. 6.

The exemplary process shown in FIG. 5 may facilitate analysis and/or control of the chemical and/or biological process since the number of process parameters in a model of the chemical and/or biological process is reduced to include the process parameters that may be more likely to affect the at least one process output value than the excluded process parameters (e.g., compare FIGS. 6 and 8). For example, the output results in step S60 may facilitate the user (e.g., data owner, process expert, etc.) to interpret what might be causal information and what might be spurious correlations in the model(s) of the chemical and/or biological process.

Variations

In the exemplary embodiments described above, the p-loadings and their standard errors are mentioned as examples of the correlation values and the confidence values calculated in step S20 of FIG. 5. In further exemplary embodiments, one of the following values and their confidence values (e.g., standard errors) may be calculated as the correlation values and the confidence values in step S20 of FIG. 5.

p(corr)

P(corr) may represent the calculated correlation between the scaled X variables and the score vector in an OPLS model. Thus, for a scaled X variable, P(corr) may be:

pcorr(var A)=sum(XVarWS(var Art)*t)/sqrt(SS(t)*SS (XVarWS(var A))

where XVarWS(var A) may be a vector with scaled values of a variable A, t may be a score vector, pcorr(var A) may be the calculated correlation between the scaled X values of variable A and the score vector, and SS may be sum of squares.

w w may represent the weights that combine the X variables (e.g., first dimension) or the residuals of the X variables (e.g., subsequent dimensions) to form the scores t in a PLS or OPLS model. These weights may be selected so as to maximize the covariance between the X scores matrix T and the Y scores matrix U, thereby indirectly the covariance between the X scores matrix T and the response matrix Y.

w*

For every PLS component, the W*'s may represent the weights that combine the original X variables (not their residuals as with w) to form the scores t.

W* may be computed as follows:

$$W^* = W(P'W)-1$$

where W may be the weights that combine the X variables (e.g., first dimension) or the residuals of the X variables (e.g., subsequent dimensions) to form the scores t in a PLS model as stated above and P may be the X loading matrix.

CoeffCS

CoeffCS may be the coefficients when the predictor matrix X is scaled and centered and the response matrix Y is scaled. These coefficients may be used for interpreting the influence of the X variables on the response matrix Y. The scaling weights may be those selected in the workset (e.g., a full copy of one or more datasets, or a subset selection of parts of one or more datasets, which may be the basis for model calculations), usually to give the X and Y variables unit variance (e.g., autoscaling).

The centered and scaled coefficients may be expressed according to the following formula:

$$y * ws_m = \bar{y} * ws_m + b_k(x_k - \bar{x}_k) * ws_k + \ldots \ldots +$$
$$b_{kk}(z_k^2 * ws_k^2 - m_{kk}) * v_k + \ldots \ldots + b_{jk}(z_j * z_k * ws_j * ws_k - m_{jk}) * v_{jk} + \ldots$$

where $ws_m$ may be scaling weights of response ym and $ws_k$ may be scaling weights of variable $x_k$, $m_{kk}$ may be average of $z_k^2$, $m_{jk}$ may be average of $z_j*z_k$, $v_k$ may be scaling weight of $z_k^2$, $v_{ij}$ may be scaling weight of $z_i*z_j$.

PRED_VIP$_{OPLS}$, TOT_VIP$_{OPLS}$, VIP$_{PLS}$

For PLS, the influence on the response matrix Y of every term ($x_k$) in the model may be computed and this influence may be called VIP (variable importance in the projection). VIP may be the sum over all model dimensions of the contributions VIN (variable influence). For a given PLS dimension, a, $(VIN)_{ak}^2$ may be equal to the squared PLS weight $(w_{ak})^2$ of that term, multiplied by the explained SS of that PLS dimension.

The accumulated (over all PLS dimensions) value may be:

$$VIP_{ak}^2 = \Sigma(VIN)_k^2$$

where the summation may be made over a=1 to A.

This value may then be divided by the total explained SS by the PLS model and multiplied by the number of terms in the model. The final VIP may be the square root of that number.

The formula can also be expressed as:

$$VIP_{PLS} = \sqrt{K \times \left(\frac{\left[\sum_{a=1}^{A}(w_a^2 \times SSY_{comp,a})\right]}{SSY_{cum}}\right)}$$

Thus, the sum of squares of all VIP's may be equal to the number of terms in the model and hence the average VIP may be equal to 1. One can compare the VIP of one term to the others. Terms with large VIP, larger than 1, may be the most relevant for explaining the response matrix Y.

For OPLA, three VIP vectors may be computed according to:

$$PRED\_VIP_{OPLS} = \sqrt{K_p \times \left(\frac{\left[\sum_{a=1}^{A_p}(P_a^2 \times SSX_{comp,a})\right]}{SSX_{cum}} + \frac{\left[\sum_{a=1}^{A_p}(P_a^2 \times SSY_{comp,a})\right]}{SSY_{cum}}\right)}$$

$$ORTH\_VIP_{OPLS} =$$

$$\sqrt{K_s \times \left(\frac{\left[\sum_{a_o=1}^{A_o}(Po_a^2 \times SSX_{comp,ao})\right]}{SSX_{cum}} + \frac{\left[\sum_{a_o=1}^{A_o}(Po_a^2 \times SSY_{comp,ao})\right]}{SSY_{cum}}\right)}$$

$$TOT\_VIP_{OPLS} =$$

$$\sqrt{\frac{K}{2} \times \left(\frac{\left[\sum_{a_o=1}^{A_o}(Po_a^2 \times SSX_{comp,ao})\right]}{SSX_{cum}} + \frac{\left[\sum_{a=1}^{A_p}(P_a^2 \times SSX_{comp,a})\right]}{SSX_{cum}} + \frac{\left[\sum_{a_o=1}^{A_o}(Po_a^2 \times SSY_{comp,ao})\right]}{SSY_{cum}} + \frac{\left[\sum_{a=1}^{A_p}(P_a^2 \times SSY_{comp,a})\right]}{SSY_{cum}}\right)}$$

In the expressions above:

PRED_VIP$_{OPLS}$ may represent the VIP value for the predictive components in an OPLS model, ORTH_VIP$_{OPLS}$ may correspond to the VIP value for the orthogonal components in an OPLS model, and TOT_VIP$_{OPLS}$ may represent the total sum of VIP for both predictive and orthogonal parts of an OPLS model.

Hardware Configuration

Figure 11:
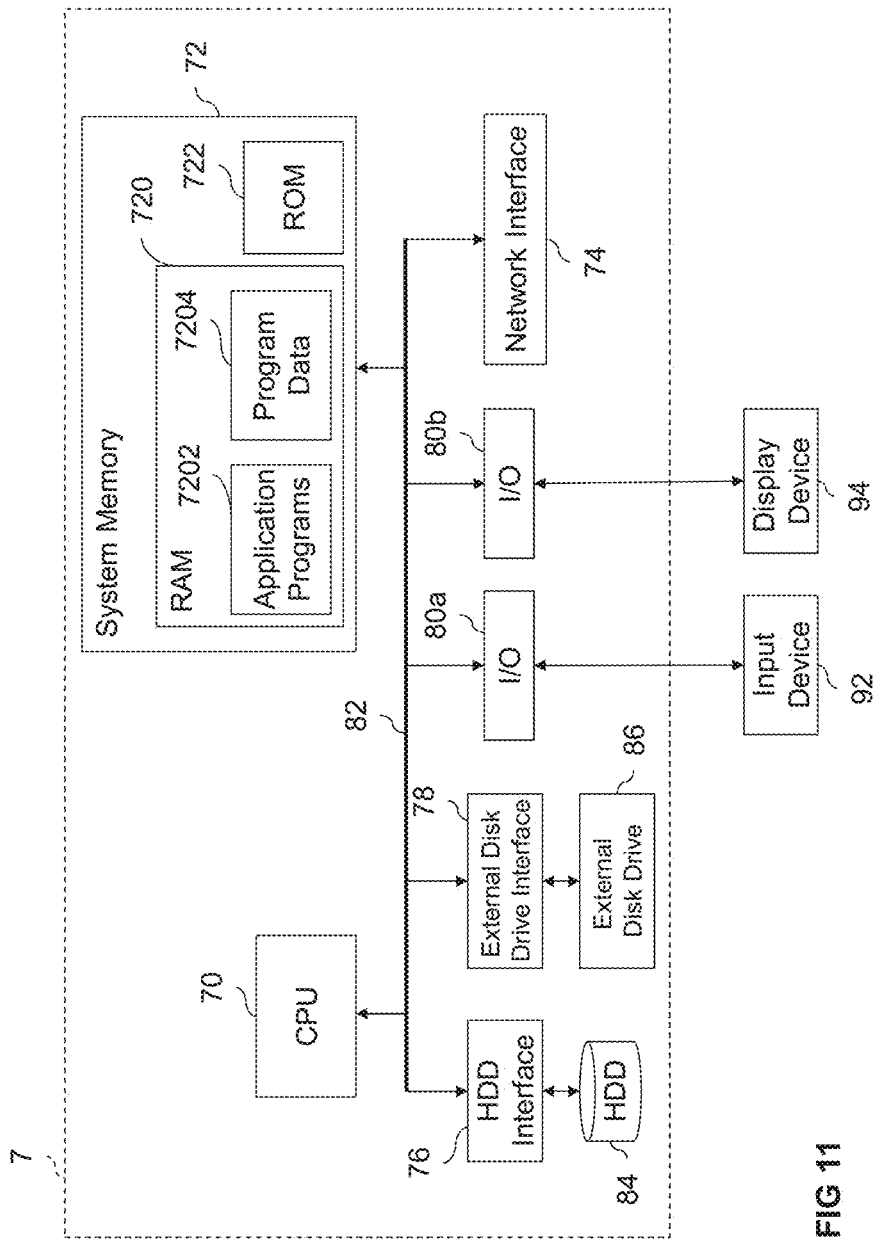
FIG. 11 shows an exemplary hardware configuration of a computer that may be used to implement at least a part of a system according to the present disclosure.

FIG. 11 shows an exemplary hardware configuration of a computer that may be used to implement at least a part of the system as described above. For example, the computing device 20 shown in FIG. 1 may be implemented with the computer 7 shown in FIG. 11. The computer 7 shown in FIG. 11 includes a central processing unit (CPU) 70, a system memory 72, a network interface 74, a hard disk drive (HDD) interface 76, an external disk drive interface 78 and input/output (I/O) interfaces 80. These components of the computer are coupled to each other via a system bus 82. The CPU 70 may perform arithmetic, logic and/or control operations by accessing the system memory 72. The system memory 72 may store information and/or instructions for use in combination with the CPU 70. The system memory 72 may include volatile and non-volatile memory, such as a random access memory (RAM) 720 and a read only memory (ROM) 722. A basic input/output system (BIOS) containing the basic routines that helps to transfer information between elements within the computer 7, such as during start-up, may be stored in the ROM 722. The system bus 82 may be any of several types of bus structures including a memory bus or memory controller, a peripheral bus, and a local bus using any of a variety of bus architectures.

The computer may include a network interface 74 for communicating with other computers and/or devices via a network.

Further, the computer may include a hard disk drive (HDD) 84 for reading from and writing to a hard disk (not shown), and an external disk drive 86 for reading from or writing to a removable disk (not shown). The removable disk may be a magnetic disk for a magnetic disk drive or an optical disk such as a CD ROM for an optical disk drive. The HDD 84 and the external disk drive 86 are connected to the system bus 82 by a HDD interface 76 and an external disk drive interface 78, respectively. The drives and their associated computer-readable media provide non-volatile storage of computer-readable instructions, data structures, program modules and other data for the general-purpose computer. The data structures may include relevant data for the implementation of the exemplary method and its variations as described herein. The relevant data may be organized in a database, for example a relational or object database.

Although the exemplary environment described herein employs a hard disk (not shown) and an external disk (not shown), it should be appreciated by those skilled in the art that other types of computer readable media which can store data that is accessible by a computer, such as magnetic cassettes, flash memory cards, digital video disks, random access memories, read only memories, and the like, may also be used in the exemplary operating environment.

A number of program modules may be stored on the hard disk, external disk, ROM 722 or RAM 720, including an operating system (not shown), one or more application programs 7202, other program modules (not shown), and program data 7204. The application programs may include at least a part of the functionality as described above.

The computer 7 may be connected to an input device 92 such as mouse and/or keyboard and a display device 94 such as liquid crystal display, via corresponding I/O interfaces 80a and 80b as well as the system bus 82. In case the computer 7 is implemented as a tablet computer, for example, a touch panel that displays information and that receives input may be connected to the computer 7 via a corresponding I/O interface and the system bus 82. Further, in some examples, although not shown in FIG. 11, the computer 7 may further be connected to a printer and/or an imaging device such as a camera, via corresponding I/O interfaces and the system bus 82.

In addition or as an alternative to an implementation using a computer 7 as shown in FIG. 11, a part or all of the functionality of the exemplary embodiments described herein may be implemented as one or more hardware circuits. Examples of such hardware circuits may include but are not limited to: Large Scale Integration (LSI), Reduced Instruction Set Circuits (RISC), Application Specific Integrated Circuit (ASIC) and Field Programmable Gate Array (FPGA).

The invention claimed is:

1. A computer-implemented method for analyzing data obtained with respect to a chemical and/or biological process, the method comprising:
   obtaining a result of statistical data analysis on a data set including the data obtained with respect to the chemical and/or biological process, wherein:
      the chemical and/or biological process is carried out in a plurality of batch processes having a finite duration,
      values of process parameters relating to the chemical and/or biological process are obtained at a plurality of time points during each of the plurality of batch processes, each time point in one of the plurality of batch processes having corresponding time points in other ones of the plurality of batch processes, wherein the process parameters comprise temperature, pressure, pH, agitation, flow of a gas, flow of a liquid, or an amount of a particular substance,
      at least one process output value is obtained at or after an end of each of the plurality of batch processes, wherein the output value comprises yield in a chemical process, titer in a biological process, or amount of a by-product,
      the data set includes, for each of the plurality of batch processes, the values of the process parameters and the at least one process output value,
      the data set serves as a training set for a model stored in one or more non-transitory computer-readable media and configured to receive the values of the process parameters and predict the at least one process output value comprising yield in a chemical process, titer in a biological process, or amount of a by-product; and
      the result of the statistical data analysis includes, for the values of each process parameter obtained at each group of corresponding time points during the plurality of batch processes, a correlation value and a confidence value corresponding to a confidence interval of the correlation value, the correlation value indicating a correlation between:
         the values of the process parameter obtained at the group of corresponding time points during the plurality of batch processes, and
         the at least one process output value comprising yield in a chemical process, titer in a biological process, or amount of a by-product predicted using the model;
   calculating, for the values of each process parameter obtained at each group of corresponding time points during the plurality of batch processes, a ratio of the correlation value to the confidence value;
   calculating, for each of the process parameters, an average of absolute values of the ratios calculated for the values of the process parameter obtained at different groups of the corresponding time points during the plurality of batch processes;
   excluding, from the data set serving as the training set for the model, the values of one of the process parameters having a smallest one of the averages calculated for the process parameters;
   iterating, until at least one specified condition is met, the steps of obtaining the result of the statistical data analysis, calculating the ratio of the correlation value to the confidence value, calculating the average of the absolute values of the ratios and excluding the values of the one of the process parameters from the data set serving as the training set for the model, thereby reducing the data set serving as the training set for the model;

with one or more computing devices, training the model with the reduced data set serving as the training set for the model, wherein the excluded values are not included as part of the training, thereby reducing a size of the data set stored in the one or more non-transitory computer-readable media by the one or more computing devices and serving as the training set for the model; and controlling a subsequent iteration of the chemical and/or biological process based on the model trained with the reduced data set.

2. The method according to claim 1, wherein the at least one specified condition includes a condition that the data set includes the values of a single process parameter after performing the step of excluding the values of the one of the process parameters.

3. The method according to claim 1, wherein the result of the statistical data analysis includes:
a model representing relationships between the process parameters and the at least one process output value; and
at least one quality measure of the model.

4. The method according to claim 3, wherein the correlation value for the values of each process parameter obtained at each group of corresponding time points during the plurality of batch processes is obtained by calculating a correlation between:
the values of the process parameter obtained at the group of corresponding time points during the plurality of batch processes, and
at least one predicted process output value that is predicted using the model.

5. The method according to claim 3, further comprising:
outputting the at least one quality measure of the model included in the result of the statistical data analysis obtained in each iteration of the steps of obtaining the result of the statistical data analysis, calculating the ratio of the correlation value to the confidence value, calculating the average of the absolute values of the ratios and excluding the values of the one of the process parameters.

6. The method according to claim 3, wherein the at least one specified condition includes a condition defined according to the at least one quality measure of the model.

7. The method according to claim 3, wherein the statistical data analysis is partial least squares, PLS, or orthogonal partial least squares, OPLS;
wherein the at least one quality measure of the model may include: goodness of fit or a goodness of prediction.

8. The method according to claim 7, wherein the values of each process parameter obtained at each group of corresponding time points during the plurality of batch processes correspond to a variable of a predictor matrix X of PLS or OPLS;
wherein the at least one process output value corresponds to at least one variable of a response matrix Y of PLS or OPLS; and
wherein the correlation value may be:
a p-loading value of the corresponding variable of the predictor matrix X,
a value indicating a calculated correlation between scaled values of the corresponding variable of the predictor matrix X and X-scores T of OPLS,
a weight value of the corresponding variable of the predictor matrix X, used for obtaining the X-scores T from X-residuals E of PLS or OPLS,
a weight value of the corresponding variable of the predictor matrix X, used for obtaining the X-scores T from the variables of the predictor matrix X,
a centered and scaled coefficient of the corresponding variable of the predictor matrix X, or
a variable importance in projection, VIP, value of the corresponding variable of the predictor matrix X, the VIP value indicating an influence on the response matrix Y of the corresponding variable of the predictor matrix X.

9. A computer program product comprising computer-readable instructions that, when loaded and run on a computer, cause the computer to perform operations for analyzing data obtained with respect to a chemical and/or biological process, the operations comprising:
obtaining a result of statistical data analysis on a data set including the data obtained with respect to the chemical and/or biological process, wherein:
the chemical and/or biological process is carried out in a plurality of batch processes having a finite duration,
values of process parameters relating to the chemical and/or biological process are obtained at a plurality of time points during each of the plurality of batch processes, each time point in one of the plurality of batch processes having corresponding time points in other ones of the plurality of batch processes, wherein the process parameters comprise temperature, pressure, pH, agitation, flow of a gas, flow of a liquid, or an amount of a particular substance,
at least one process output value is obtained at or after an end of each of the plurality of batch processes, wherein the output value comprises yield in a chemical process, titer in a biological process, or amount of a by-product,
the data set includes, for each of the plurality of batch processes, the values of the process parameters and the at least one process output value,
the data set serves as a training set for a partial least squares (PLS) or orthogonal partial least squares (OPLS) model stored in one or more non-transitory computer-readable media and configured to receive the values of the process parameters and predict the at least one process output value comprising yield in a chemical process, titer in a biological process, or amount of a by-product; and
the result of the statistical data analysis includes, for the values of each process parameter obtained at each group of corresponding time points during the plurality of batch processes, a correlation value and a confidence value corresponding to a confidence interval of the correlation value, the correlation value indicating a correlation between:
the values of the process parameter obtained at the group of corresponding time points during the plurality of batch processes, and
the at least one process output value comprising yield in a chemical process, titer in a biological process, or amount of a by-product predicted using the model;
calculating, for the values of each process parameter obtained at each group of corresponding time points during the plurality of batch processes, a ratio of the correlation value to the confidence value;

calculating, for each of the process parameters, an average of absolute values of the ratios calculated for the values of the process parameter obtained at different groups of the corresponding time points during the plurality of batch processes;

excluding, from the data set serving as the training set for the model, the values of one of the process parameters having a smallest one of the averages calculated for the process parameters;

iterating, until at least one specified condition is met, the steps of obtaining the result of the statistical data analysis, calculating the ratio of the correlation value to the confidence value, calculating the average of the absolute values of the ratios and excluding the values of the one of the process parameters from the data set serving as the training set for the model, thereby reducing the data set serving as the training set for the model;

with one or more computing devices, training the model with the reduced data set serving as the training set for the model, wherein the excluded values are not included as part of the training, thereby reducing a size of the data set stored in the one or more non-transitory computer-readable media by the one or more computing devices and serving as the training set for the model; and controlling a subsequent iteration of the chemical and/or biological process based on the model trained with the reduced data set.

10. A system for analyzing data obtained with respect to a chemical and/or biological process, the system comprising:
a non-transitory storage medium storing a data set including the data obtained with respect to the chemical and/or biological process, wherein:
the chemical and/or biological process is carried out in a plurality of batch processes having a finite duration,
values of process parameters relating to the chemical and/or biological process are obtained at a plurality of time points during each of the plurality of batch processes, each time point in one of the plurality of batch processes having corresponding time points in other ones of the plurality of batch processes, wherein the process parameters comprise temperature, pressure, pH, agitation, flow of a gas, flow of a liquid, or an amount of a particular substance,
at least one process output value is obtained at or after an end of each of the plurality of batch processes, and
the data set includes, for each of the plurality of batch processes, the values of the process parameters and the at least one process output value, and
the data set serves as a training set for a model stored in one or more non-transitory computer-readable media and configured to receive the values of the process parameters and predict the at least one process output value; and
a processor configured to:
obtain a result of statistical data analysis on the data set, the result of the statistical data analysis including, for the values of each process parameter obtained at each group of corresponding time points during the plurality of batch processes, a correlation value and a confidence value corresponding to a confidence interval of the correlation value, the correlation value indicating a correlation between:
the values of the process parameter obtained at the group of corresponding time points during the plurality of batch processes, and
the at least one process output value predicted using the model;
calculate, for the values of each process parameter obtained at each group of corresponding time points during the plurality of batch processes, a ratio of the correlation value to the confidence value;
calculate, for each of the process parameters, an average of absolute values of the ratios calculated for the values of the process parameter obtained at different groups of the corresponding time points during the plurality of batch processes;
exclude, from the data set serving as the training set for the model, the values of one of the process parameters having a smallest one of the averages calculated for the process parameters;
iterate, until at least one specified condition is met, the steps to obtain the result of the statistical data analysis, calculate the ratio of the correlation value to the confidence value, calculate the average of the absolute values of the ratios and exclude the values of the one of the process parameters from the data set serving as the training set for the model, thereby reducing the data set serving as the training set for the model;
with one or more computing devices, train the model with the reduced data set serving as the training set for the model, wherein the excluded values are not included as part of the training thereby reducing a size of the data set stored in the one or more non-transitory computer-readable media by the one or more computing devices serving as the training set for the model; and
with the model, predict yield in a chemical process, titer in a biological process, or amount of a by-product; and
controlling a subsequent iteration of the chemical and/or biological process based on the model trained with the reduced data set.

11. The system according to claim 10, wherein the at least one specified condition includes a condition that the data set includes the values of a single process parameter after performing the step of excluding the values of the one of the process parameters.

12. The system according to claim 10, wherein the result of the statistical data analysis includes:
a model representing relationships between the process parameters and the at least one process output value; and
at least one quality measure of the model; and
wherein the processor may be further configured to:
output the at least one quality measure of the model included in the result of the statistical data analysis obtained in each iteration of the steps to obtain the result of the statistical data analysis, calculate the ratio of the correlation value to the confidence value, calculate the average of the absolute values of the ratios and exclude the values of the one of the process parameters.

13. The system according to claim 12, wherein the at least one specified condition includes a condition defined according to the at least one quality measure of the model; and
wherein the correlation value for the values of each process parameter obtained at each group of corresponding time points during the plurality of batch processes may be obtained by calculating a correlation between:

the values of the process parameter obtained at the group of corresponding time points during the plurality of batch processes, and at least one predicted process output value that is predicted using the model.

14. The system according to claim 12, wherein the statistical data analysis is partial least squares, PLS, or orthogonal partial least squares, OPLS; and wherein the at least one quality measure of the model may include: a goodness of fit or a goodness of prediction.

15. The system according to claim 14, wherein the values of each process parameter obtained at each group of corresponding time points during the plurality of batch processes correspond to a variable of a predictor matrix X of PLS or OPLS;

wherein the at least one process output value corresponds to at least one variable of a response matrix Y of PLS or OPLS; and wherein the correlation value may be:
a p-loading value of the corresponding variable of the predictor matrix X, a value indicating a calculated correlation between scaled values of the corresponding variable of the predictor matrix X and X-scores T of OPLS, a weight value of the corresponding variable of the predictor matrix X, used for obtaining X-scores T from X-residuals E, a weight value of the corresponding variable of the predictor matrix X, used for obtaining X-scores T from the variables of the predictor matrix X, a centered and scaled coefficient of the corresponding variable of the predictor matrix X, or a variable importance in projection, VIP, value of the corresponding variable of the predictor matrix X, the VIP value indicating an influence on the response matrix Y of the corresponding variable of the predictor matrix X.

* * * * *